US009029320B2

(12) United States Patent
Bentz et al.

(10) Patent No.: US 9,029,320 B2
(45) Date of Patent: May 12, 2015

(54) FORMULATIONS AND METHODS FOR WEIGHT LOSS AND BODY CONTOURING

(71) Applicant: Red Mountain Med Spa, LLC, Scottsdale, AZ (US)

(72) Inventors: Mark Bentz, Scottsdale, AZ (US); Suzanne Bentz, Scottsdale, AZ (US); Riccardo Roscetti, Boynton Beach, FL (US); M. Socorro Parra Arenas, Coconut Creek, FL (US)

(73) Assignee: Red Mountain Med Spa, LLC, Scottsdale, AZ (US)

( * ) Notice: Subject to any disclaimer, the term of this patent is extended or adjusted under 35 U.S.C. 154(b) by 0 days.

(21) Appl. No.: 13/975,619

(22) Filed: Aug. 26, 2013

(65) Prior Publication Data
US 2014/0057839 A1    Feb. 27, 2014

Related U.S. Application Data

(60) Provisional application No. 61/693,495, filed on Aug. 27, 2012.

(51) Int. Cl.

| | |
|---|---|
| *A61K 38/00* | (2006.01) |
| *A61K 38/22* | (2006.01) |
| *A61K 38/16* | (2006.01) |
| *A61K 38/24* | (2006.01) |
| *A61K 31/05* | (2006.01) |
| *A61K 9/00* | (2006.01) |
| *A61K 9/20* | (2006.01) |
| *A61K 47/00* | (2006.01) |

(52) U.S. Cl.
CPC ............... *A61K 38/24* (2013.01); *A61K 31/05* (2013.01); *A61K 9/006* (2013.01); *A61K 9/2072* (2013.01); *A61K 47/00* (2013.01)

(58) Field of Classification Search
None
See application file for complete search history.

(56) References Cited

U.S. PATENT DOCUMENTS

| | | | |
|---|---|---|---|
| 6,248,363 B1 | 6/2001 | Patel et al. | |
| 7,605,122 B2 | 10/2009 | Tuntland | |
| 2005/0158376 A1 | 7/2005 | Sardi et al. | |
| 2009/0181883 A1 | 7/2009 | Tuntland | |
| 2010/0081608 A1 | 4/2010 | Belluscio | |

OTHER PUBLICATIONS

Hamilton et al. 2004. Obesity Rev. 5:217-232.*
Lovejoy et al. 2012. Int J of Obesity. 36:385-386.*
Mosier 2011. Thesis, Univ. Toledo Digital Repository utdr.utoledo.edu/graduate-projects, p. 1-63.*
Restriction Requirement dated Mar. 12, 2014 in U.S. Appl. No. 14/179,937.
Office Action dated Jun. 12, 2014 in U.S. Appl. No. 14/179,937.
Rivera et al., "Long-term resveratrol administration reduces metabolic disturbances and lowers blood pressure in obese Zucker rats," 2009, Spain, Biochemical Pharmacology, 77:1 053-1 063.
Kruse et al. "Compression Characterization and Lubricant Sensitivity of Orally Disintegrating Tablets Based on Ludiflash" 2008, Germany, APV World Meeting. 7.
News Release, "Small Molecule Increases Lifespan and "Healthspan" of Obese Mice," Harvard Medical School Office of Public Affairs, Nov. 1, 2006.
Devitt, Terry, "Agent in Red Wine Found to Keep Hearts Young," Board of Regents of the University of Wisconsin System, Jun. 4, 2008.
Barger, Jamie L., "A Low Dose of Dietary Resveratrol Partially Mimics Caloric Restriction and Retards Aging Parameters in Mice," Plos One, vol. 3, Issue 6, Jun. 2008.
Timmers, Silvie, "Calorie Restriction-like Effects of 30 Days of Resveratrol Supplementation on Energy Metabolism and Metabolic Profile in Obese Humans," Cell Press, Elsevier Inc., pp. 612-622, Nov. 2, 2011.
Harvard Medical School Study, "Red Wine Extract Key to Longer Life!" Harvard Medical School, 2007.
Notice of Allowance dated Sep. 16, 2014 in U.S. Appl. No. 14/179,937.

\* cited by examiner

*Primary Examiner* — Shulamith H Shafer
(74) *Attorney, Agent, or Firm* — Snell & Wilmer L.L.P.

(57) ABSTRACT

Formulations and methods for weight loss and body contouring are disclosed. An illustrative formulation comprises human chorionic gonadotrophin (hCG) and resveratrol. An illustrative method for weight loss and body contouring comprises administering hCG and resveratrol sublingually.

7 Claims, No Drawings

FORMULATIONS AND METHODS FOR WEIGHT LOSS AND BODY CONTOURING

CROSS REFERENCE TO RELATED APPLICATION

This application claims priority to, and the benefit of, U.S. Provisional Application Ser. No. 61/693,495 entitled "FORMULATION AND METHODS FOR WEIGHT LOSS AND BODY CONTOURING," filed Aug. 27, 2012, which is incorporated herein by reference in its entirety for all purposes.

FIELD

The present disclosure generally relates to health care, and more particularly, to formulations and methods for weight loss and body contouring.

BACKGROUND

People are increasingly concerned with physical appearances and health, which has led to a massive market for medical weight-loss, beauty, and anti-aging treatments. More traditional exercise regimens and/or diets have not been sufficiently successful for many people, so a need exists for formulations that promote rapid weight loss and body contouring.

Moreover, obesity in America has reached near "epidemic" proportions with 66% of Americans considered overweight or obese. There is a paucity of effective weight loss treatments. Many subjects are not candidates for risky and aggressive gastric bypass or gastric banding obesity surgery. Thus, a need exists for safe, non-surgical weight loss therapies.

SUMMARY

The present disclosure comprises formulations and methods for weight loss and body contouring. An illustrative formulation comprises human chorionic gonadotrophin (hCG) and an antioxidant. Illustrative antioxidants include flavonoids such as resveratrol. An illustrative method for weight loss and body contouring comprises prescribing or administering a biological hormone and an antioxidant orally (e.g., sublingually in the form of a liquid, tablet, lozenge, capsule, or spray), or transdermally (e.g., in the form of a cream, lotion, spray, solution, or skin patch). An illustrative method further comprises an exercise regimen and/or a low or very low calorie diet and a sustained maintenance program.

DETAILED DESCRIPTION

The disclosure includes formulations and methods for weight loss and body contouring. Persons skilled in the art will readily appreciate that various aspects of the disclosure may be realized by any number of formulations and methods configured to perform the intended functions. Stated differently, other formulations and methods may be incorporated herein to perform the intended functions. Although the present disclosure may be in connection with various medical principles and beliefs, the present disclosure should not be bound by theory.

The term "approximately," as used in this specification and appended claims, refers to plus or minus 5% of the value given. The term "about," as used in this specification and appended claims, refers to plus or minus 10% of the value given. Weight percentages provided herein are based on a dosage of 350 IU/25 mg.

An illustrative formulation comprises one or more of: (i) a biological hormone; (ii) an antioxidant; and (iii) one or more optional excipients.

In various embodiments, and without wishing to be bound by theory, it is believed that the biological hormone may serve to assist in weight loss by targeting stored body fat for metabolism. It may further assist in decreasing hunger and enhancing "well-being", while following a low calorie diet. The biological hormone may further provide regulation of the hypothalamus which "resets" the hunger center, thereby decreasing the desire to overeat. An illustrative biological hormone comprises human chorionic gonadotrophin (hCG), yet other hormones are included within the scope of the disclosure.

Persons skilled in the art will readily appreciate that a variety of antioxidants or free radical scavengers are suitable for use in connection with the present disclosure. In general, the term "antioxidant" as used herein includes any nutrient or chemical that reacts with and neutralizes oxidants, free radicals or chemicals that release free radicals, or otherwise prevents or minimizes damage to molecular structures such as DNA, is suitable for use in connection with the present disclosure. By way of example, vitamins A, C, E and B, beta-carotene, and selenium are all contemplated for use in connection with the present disclosure.

Other illustrative antioxidants comprise flavonoids, including bioflavonoid antioxidants such as resveratrol. In illustrative embodiments, resveratrol serves to counter the negative effects of a high calorie diet loaded with trans fats. Without wishing to be bound by theory, it is believed that resveratrol produces a gene activation profile similar to a calorie-restricted diet. Weight loss occurs naturally with a calorie-restricted diet. Therefore, since the gene activation profile is similar to a calorie-restricted diet, weight loss should occur. Again, without wishing to be bound by theory, it is believed that resveratrol increases mitochondria production, thereby increasing the body's ability to burn nutrients and fats into energy and accelerating the body's metabolism, which in turn helps to burn unnecessary fats before they get stored in the body and affect health and weight.

An illustrative formulation comprises from about 0.001 to about 0.1%, or approximately 0.01% by weight biological hormone. An illustrative formulation further comprises from about 1 to about 10%, or approximately 6% by weight antioxidant. The balance of the formulation can be comprised of one or more optional excipients. Optional excipients, for example fillers, lubricants, disintegrants, flavorants, sweetening agents, medicants, preservatives, and/or colorants, may be present in an amount of up to about 99% by weight.

The term "filler" as used herein, is intended to mean inert substances used as fillers, glidants, diluents or bulking agents to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

Fillers, as used herein, can be in granulated, compacted or agglomerated form, and can be directly compressible; such as, directly compressible mannitol, directly compressible sorbitol, directly compressible maltitol, directly compressible lactose, directly compressible sucrose, directly compressible xylose, directly compressible trehalose, directly compressible dextrose, directly compressible lactose, directly compressible microcrystalline cellulose and the like, and combinations thereof. Lactose monohydrate spray dry (agglomerated form) can be used in this formulation as a directly compressible filler. One or more fillers can be present in an illustrative formulation in an amount of from about 5 to about 20%, or approximately 10% by weight.

The term "lubricant", as used herein, is intended to mean substances used in tablet formulations to reduce friction during tablet compression. Such compounds include, by way of example and without limitation, sodium stearyl fumarate, calcium stearate, magnesium stearate, mineral oil, stearic acid, zinc stearate, combinations thereof and other such materials known to those of ordinary skill in the art. One or more lubricants can be present in an illustrative formulation in an amount of from about 1.5 to about 6%, or approximately 3% by weight.

The term "disintegrant," as used herein, is intended to mean a compound used in solid dosage forms to promote the disruption of the solid mass into smaller particles which are more readily dispersed or dissolved. Exemplary disintegrants include, by way of example and without limitation, Pharmaburst® 500 (SPI Pharma, Inc.) (believed to be comprised of sugar alcohols (e.g., mannitol, maltitol, sorbitol, xylitol, lactitol, and isomalt), disintegrants (e.g., croscarmellose and crospovidone) and flow agents (e.g., silicon dioxide)), crospovidone (e.g., Polyplasdone® XL10), croscarmellose (ac di sol), starches such as corn starch, potato starch, pregelatinized and modified starches thereof, sweeteners, clays, such as bentonite, microcrystalline cellulose (e.g., Avicel™), carsium (e.g., Amberlite™), alginates, sodium starch glycolate, gums such as agar, guar, locust bean, karaya, pectin, tragacanth, combinations thereof and other such materials known to those of ordinary skill in the art. In some embodiments, a disintegrant can be mixed with one or more directly compressible fillers as directly compressible mannitol, directly compressible sorbitol, and directly compressible microcrystalline cellulose. One or more disintegrants can be present in an illustrative formulation in an amount of from about 60 to about 80%, or approximately 70% by weight.

Suitable flavorants can include, for example, flavors, such as, natural flavors, artificial flavors, and combinations thereof. Non-limiting examples of flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Suitable flavoring agents also include, for example, artificial, natural and synthetic fruit flavors such as vanilla, citrus oils (e.g., lemon, orange, lime, and grapefruit), and fruit essences (e.g., apple, pear, peach, grape, strawberry, raspberry, cherry, plum, pineapple, and apricot), and the like, and combinations thereof. One or more flavorants can be present in an illustrative formulation in an amount of from about 5 to about 20%, or approximately 10% by weight.

Suitable sweetening agents include nutritive sweeteners such as sucrose, glucose, fructose, glucose, trehalose, galactose, mannitol, sorbitol, xylitol and intensive sweeteners such as aspartame, acesulfame K, sucralose and NHDC. One or more sweetening agents can be present in an illustrative formulation in an amount of from about 0.02 to about 0.5%, or approximately 0.12% by weight.

In accordance with illustrative embodiments, an oral disintegrating tablet manufactured according to the methods described herein has an average sublingual disintegration time of less than approximately 60 seconds at 37° C., or from approximately 30 to approximately 40 seconds at 37° C.

Table 1 sets forth an example of a 350 IU/25 mg oral disintegrating tablet in accordance with various embodiments.

TABLE 1

| Ingredient | Weight % | Weight (mg) |
|---|---|---|
| hCG Powder | 0.01 | 0.003 |
| Resveratrol 98% Powder | 6.00 | 1.50 |
| Lactose Monohydrate (spray-dried) | 9.59 | 2.40 |
| Sodium Stearyl Fumarate | 3.00 | 0.75 |
| Pharmaburst ® 500 | 71.7 | 17.93 |
| Natural Peppermint Flavor | 9.59 | 2.40 |
| Sucralose | 0.12 | 0.03 |

The oral disintegrating tablet set forth in Table 1 can be manufactured by (i) accurately weighing out all the powders; (ii) sieving the powders through #40 sieve in order to homogenize the particle size; (iii) mixing the powders together using a V-blender for the appropriate mixing time (e.g., 1 hour for a batch size of 10,000 tablets); and (iv) compressing the mixture from step (iii) to form a tablet.

By way of example and without limitation, to form a tablet as in step (iv) above, the materials can be deposited into a cavity, and one or more punch members can then be advanced into the cavity and brought into intimate contact with the material to be pressed, whereupon compressive force is applied. The material is thus forced into conformity with the shape of the punches and the cavity. Hundreds, and even thousands, of tablets per minute can be formed in this fashion.

One of the most common challenges associated with tablet formulation in the prior art is proper flow of the powder formula. In the prior art, powder flow is often improved by incorporating one or more flow agents, such as fumed silicon dioxide or silica gel. However, such flow agents often have a negative effect on the tablet hardness, necessitating an increased weight percentage of fillers. In connection with the present disclosure, it was surprisingly found that lactose monohydrate (spray dried) alone in an amount equal to or about that set forth in Table 1, without any additional flow agent, yielded a finished product with better quality properties. The addition of the lactose monohydrate provided for the proper flow, improved tablet hardness, and did not interfere with the fast tablet disintegration. Thus, some embodiments of the present disclosure do not comprise silicon dioxide, colloidal silica, gel silica, precipitated silica, or any other flow agent, or do not comprise any such flow agent in an amount greater than approximately 1.05% by weight, or greater than approximately 0.5% by weight, or greater than approximately 0.1% by weight.

Illustrative methods for weight loss and body contouring comprise prescribing or administering a biological hormone and an antioxidant orally (e.g., sublingually in the form of a liquid, tablet, lozenge, capsule, or spray), or transdermally (e.g., in the form of a cream, lotion, spray, solution, or skin patch).

One such method, in accordance with various embodiments, comprises (i) sublingually prescribing or administering a tablet comprising a biological hormone and an antioxidant; and (ii) instructing a subject to not chew or swallow the tablet; and (iii) instructing the subject to let the tablet dissolve completely; and (iv) instructing the subject to continue to leave the tablet in mouth for an additional 1-2 minutes, and then swallow; and (v) instructing the subject to not eat, drink, brush teeth or put anything in mouth for an additional 15-20 minutes to allow the tablet to absorb into the subject's oral mucosa.

An illustrative method further comprises an exercise regimen and/or a low or very low calorie diet and a sustained maintenance program. One such method, in accordance with various embodiments, comprises a "load phase" on days 1 and 2, during which a formulation in accordance with various embodiments is taken by a subject in the morning and/or evening as directed, and the subject eats as much as he/she wants, especially foods that are high in fat. Days 3 to 28 comprise a "diet phase," during which the subject continues taking the formulation as directed, and begins a reduced calorie diet. In response to the subject reaching his/her goal weight, he/she stops (or reduces) taking the formulation, but continues the reduced calorie diet for three additional days. After the three additional days, the subject begins a three week "maintenance phase," during which he/she can add fats and proteins to his/her diet in any quantity, but continues diet modification with no sugar and no starch.

In a clinical study, the oral disintegrating tablet set forth in Table 1 was prescribed to five subjects (A-E) for one month. Each subject had an initial weigh in, at which time the subject's body mass index ("BMI") and waist were also both measured. Each subject was then weighed weekly for four weeks, at which time the subject's BMI and waist were also both measured. Table 2 illustrates weight loss, BMI decrease, and waist measurement decrease from initial weigh in to final weigh in after four weeks.

TABLE 2

| | Subject | | | | | |
|---|---|---|---|---|---|---|
| | A | B | C | D | E | Average |
| Weight (lbs.) | 32.2 | 27.0 | 32.2 | 21.0 | 22.0 | 26.9 |
| BMI (%) | 3.90 | 3.60 | 4.40 | 2.80 | 3.30 | 3.60 |
| Waist Measurement (in.) | 3.5 | 6.5 | 3.0 | 3.5 | 3.0 | 3.9 |

No negative side effects were observed for any of the five subjects. Thus, and as supported by the data in Table 2, formulations in accordance with various embodiments can provide for safe, non-surgical weight loss therapies.

Systems and methods are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The foregoing disclosure is merely illustrative of the present disclosure and is not intended to be construed as limiting the invention. Although one or more embodiments of the invention have been described, persons skilled in the art will readily appreciate that numerous modifications could be made without departing from the spirit and scope of the present disclosure. By way of example, a formulation in accordance with the present disclosure can comprise, consist essentially of, or consisting of, any combination of the ingredients described above. As such, it should be understood that all such modifications are intended to be included within the scope of the disclosure.

We claim:

1. A method for promoting weight loss in a subject comprising:
   prescribing or administering to the subject at least one of an exercise regimen and a low calorie diet; and
   prescribing or administering to the subject a formulation for weight loss consisting essentially of:
   human chorionic gonadotrophin in an amount of from about 0.001 to about 0.1 weight percent;
   resveratrol in an amount of from about 1 to about 10 weight percent;
   lactose monohydrate (spray-dried) in an amount of from about 5 to about 20 weight percent;
   sodium stearyl fumarate in an amount of from about 1.5 to about 6 weight percent;
   a disintegrant in an amount of from about 60 to about 80 weight percent;
   a flavorant; and
   a sweetening agent,
   wherein the formulation is configured to be administered orally in the form of a tablet;
   wherein the formulation does not comprise silicon dioxide, colloidal silica, gel silica, precipitated silica, or any other flow agent, in an amount greater than approximately 1.05% by weight; and
   wherein an average disintegration time is less than approximately 60 seconds at about 37° C.

2. The method of claim 1, wherein:
   the human chorionic gonadotrophin is present in an amount of about 0.01 weight percent;
   the resveratrol is present in an amount of about 6 weight percent;
   the lactose monohydrate (spray-dried) is present in an amount of about 10 weight percent;
   the sodium stearyl fumarate is present in an amount of about 3 weight percent; and
   the disintegrant is present in an amount of about 70 weight percent.

3. The method of claim 1, wherein the flavorant comprises natural peppermint flavor.

4. The method of claim 3, wherein the flavorant comprises natural peppermint flavor in an amount of about 10 weight percent.

5. The method of claim 1, wherein the sweetening agent comprises sucralose.

6. The method of claim 5, wherein the sweetening agent comprises sucralose in an amount of about 0.1 weight percent.

7. The method of claim 1, wherein the average disintegration time is from approximately 30 seconds to approximately 40 seconds at about 37° C.

* * * * *